US00PP24631P2

(12) United States Plant Patent
Blom

(10) Patent No.: US PP24,631 P2
(45) Date of Patent: Jul. 8, 2014

(54) ***ECHINACEA* PLANT NAMED 'CLEOPATRA'**

(50) Latin Name: ***Echinacea* hybrid**
Varietal Denomination: Cleopatra

(76) Inventor: Arie Blom, Oudewater (NL)

( * ) Notice: Subject to any disclaimer, the term of this patent is extended or adjusted under 35 U.S.C. 154(b) by 190 days.

(21) Appl. No.: 13/507,852

(22) Filed: Aug. 1, 2012

(51) Int. Cl.
*A01H 5/00* (2006.01)

(52) U.S. Cl.
USPC ..... Plt./428

(58) Field of Classification Search
CPC ..... A01H 5/025
USPC ..... Plt./428
See application file for complete search history.

*Primary Examiner* — June Hwu
(74) *Attorney, Agent, or Firm* — Penny J. Aguirre

(57) ABSTRACT

A new cultivar of hybrid *Echinacea*, 'Cleopatra', characterized by its composite flowers with ray florets that are deep yellow in color and held horizontal, its very strong stems, its short plant height, and its compact plant habit.

2 Drawing Sheets

Botanical classification: *Echinacea* hybrid.
Variety denomination: 'Cleopatra'.

CROSS REFERENCE TO A RELATED APPLICATION

This application is co-pending with a U.S. Plant Patent Application filed for a plant derived from the same breeding program that is entitled *Echinacea* Plant Named 'Julia' (U.S. Plant patent application Ser. No. 13/507,851).

BACKGROUND OF THE INVENTION

The present invention relates to a new and distinct cultivar of *Echinacea* of hybrid origin and will be referred to hereafter by its cultivar name, 'Cleopatra'. 'Cleopatra' represents a new coneflower, an herbaceous perennial grown for landscape use.

The new cultivar arose from an ongoing breeding program of the Inventor's in Zuidwolde, The Netherlands. The objective of the breeding program is to develop new cultivars of classic cone-type (non-anemone type) *Echinacea* having horizontal ray florets with unique and strong colors. The new cultivar arose from open pollination of an unnamed plant from the Inventor's breeding, designated as Ec 7001-03, in summer of 2008. The male parent is unknown. 'Cleopatra' was selected as single unique plant from the resulting seedlings in July of 2010.

Asexual reproduction of the new cultivar was first accomplished by in vitro propagation in Heerhugowaard, The Netherlands in 2008 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Cleopatra' as a unique cultivar of *Echinacea*.

1. 'Cleopatra' exhibits large composite flowers with ray florets that are deep yellow in color.
2. 'Cleopatra' exhibits ray florets that are held horizontal.

3. 'Cleopatra' is short in height and exhibits a compact plant habit.
4. 'Cleopatra' exhibits very strong stems.

The female parent, designated as Ec 7001-03, differs from 'Cleopatra' in having a taller plant height and ray florets that are lighter yellow in color. The new cultivar can be most closely compared to the cultivars 'Sunrise' (U.S. Plant Pat. No. 16,235), 'CBG Cone3' (U.S. Plant Pat. No. 16,636), and 'Julia' (U.S. Plant patent Ser. No. 13/507,851). 'Sunrise' differs from 'Cleopatra' in having ray florets that are lighter yellow in color and in having taller and weaker stems. 'CBG Cone3' differs from 'Cleopatra' in having ray florets that are yellow-orange in color, held less horizontal and less overlapping, and in having taller stems. 'Julia' differs from 'Cleopatra' in having ray florets that are orange in color.

BRIEF DESCRIPTION OF THE DRAWING

The plants in the accompanying photographs depict the characteristics of a one year-old plant of 'Cleopatra' as field grown in Zuidwolde, The Netherlands. Stems were cut at ground level and placed in a vase for the photographs.

The photograph in FIG. 1 shows a group of cut stems.

Figure 1:
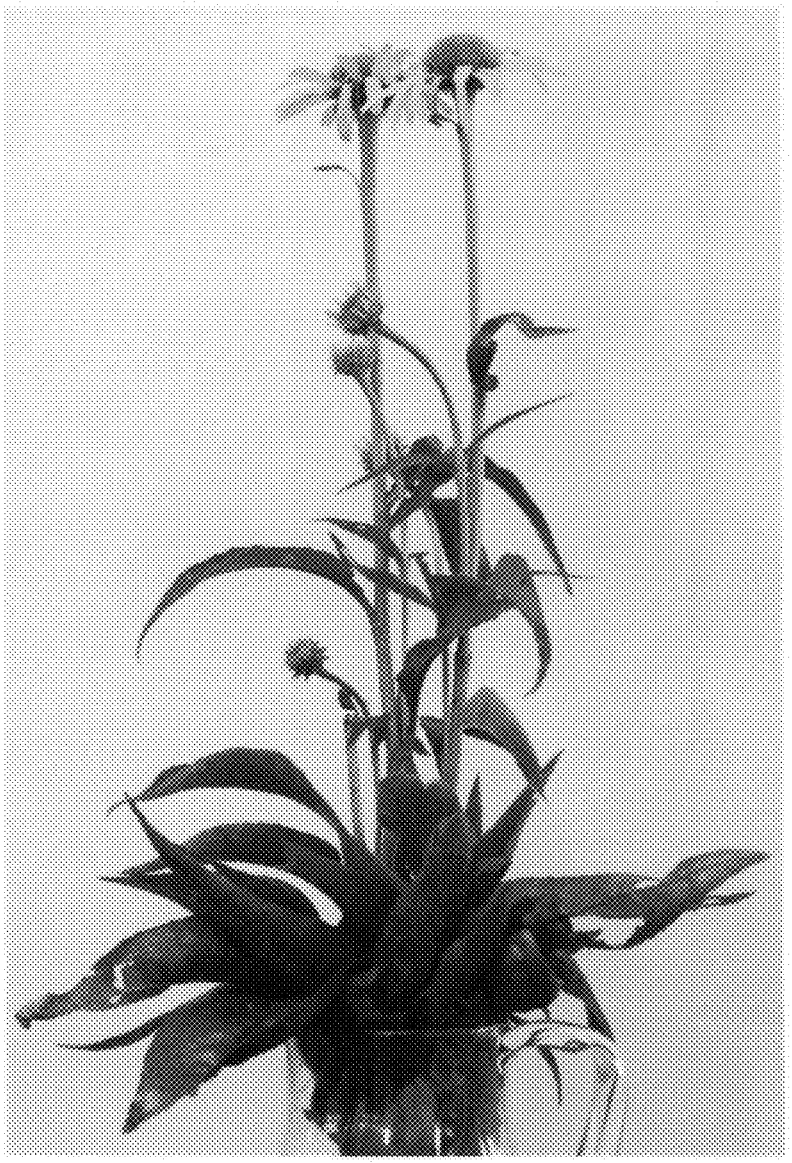
Figure 2:
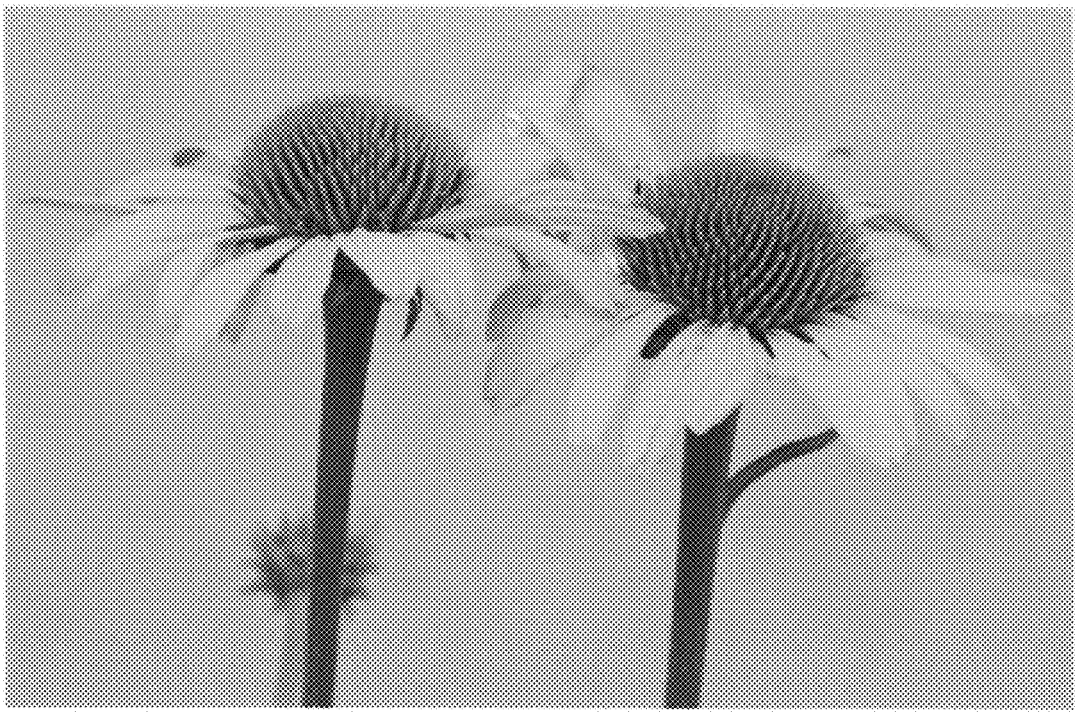

The photograph in FIG. 2 provides a close-up view of inflorescences of 'Cleopatra'.

Figure 3:
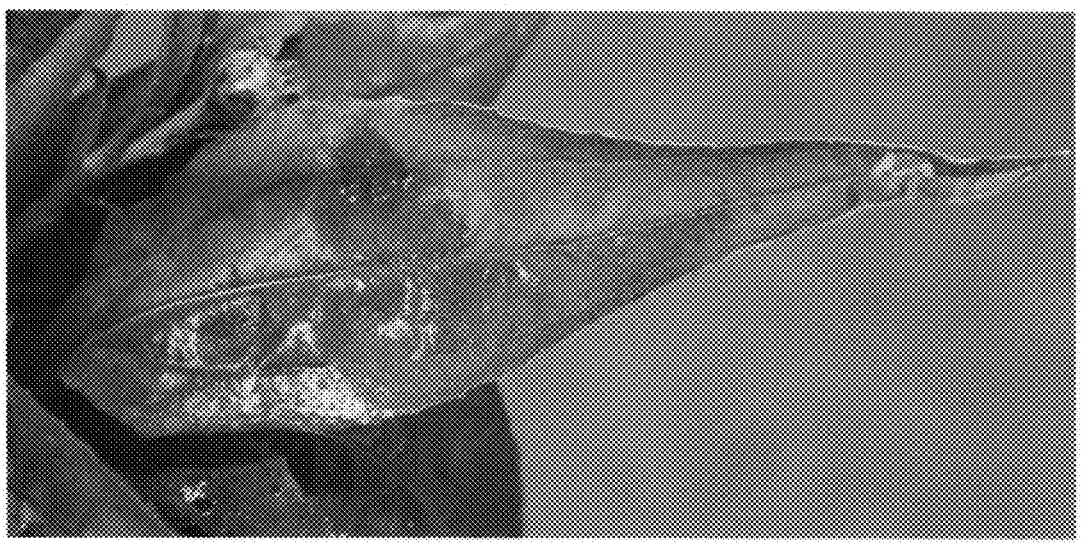

The photograph in FIG. 3 provides a close-up view of a leaf of 'Cleopatra'. The colors in the photograph may differ slightly from the color values cited in the detailed botanical description, which accurately describe the colors of the new *Echinacea*.

BOTANICAL DESCRIPTION OF THE PLANT

The following is a detailed description of one year-old plants of the new cultivar as field grown outdoors in September in Zuidwolde, The Netherlands. Plants were grown under average day temperatures ranging from 12° to 28° C. and average night temperatures of 6° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from mid June through August in The Netherlands.

*Plant habit*.—Herbaceous perennial, clump forming, upright and strong stems, compact.

*Height and spread*.—About 52.5 cm in height and 32.5 cm in spread.

*Cold hardiness*.—At least to U.S.D.A. Zones 3.

*Diseases and pests*.—No particular resistance or susceptibility to pests or diseases has been observed.

*Root description*.—Fibrous.

Growth and Propagation:

*Propagation*.—Tissue culture preferred.

*Growth rate*.—Moderately vigorous.

Stem description:

*Shape*.—Rounded.

*Stem color*.—145A.

*Stem size*.—Average of 4.5 mm in diameter and an average of 31.5 cm in height.

*Stem surface*.—Covered with a only a few short strigose hairs; 0.3 mm in length, to small to be measured with RHS-CC.

*Stem strength*.—Very strong.

*Stem number*.—Average of 4 on a one year-old plant.

*Branching*.—Un-branched.

Foliage description:

*Leaf shape*.—Narrowly ovate to ovate.

*Leaf division*.—Simple.

*Leaf base*.—Attenuate.

*Leaf apex*.—Acute to narrowly acute.

*Leaf venation*.—Pinnate, upper surface color; 137A, lower surface color; 144B.

*Leaf margins*.—Shallowly dentate.

*Leaf attachment*.—Petiolate.

*Leaf arrangement*.—Alternate.

*Internode length*.—An average of 5.8 cm.

*Leaf size*.—Average of 14.2 cm in length and 4.6 cm in width.

*Leaf color*.—Young upper surface; 137B, young lower surface; 137C, mature upper surface; N137A to N137B, mature lower surface; 147B.

*Leaf surface*.—Upper and lower surfaces are moderately glossy and very slightly rough to the touch due to being sparsely covered with very short strigose hairs; average length of 0.3 mm in length and to small to be measure with RHS-CC.

*Petioles*.—Upper stem leaves nearly sessile, average length of petioled leaves is 4.6 cm in length, v-shaped petiole is 3 mm in length and 2 mm in width, upper and lower surfaces smooth, upper surface color; 144A, lower surface color; 144B.

Flower description:

*Type*.—Terminal capitulum, heterogamous with ray florets around the head margin and disc florets in the center, forming a radiant head.

*Capitulum number*.—One terminal capitulum per branch.

*Capitulum size*.—Matures to about 2.5 cm in depth and 8.9 cm in diameter, disk size is about 2 cm in depth and 3.1 cm in diameter.

*Fragrance*.—None.

*Involucral bracts or phyllary*.—About 46 arranged in 3 overlapping rows, up to 1 cm in length and 3 mm in width, cuneate at base, narrowly acute apex, ovate to narrow ovate in shape, entire margins moderately covered with very short hairs; 0.4 mm in length and 157D in color, upper surface; smooth and 143A in color, lower surface; 137C in color, and sparsely covered with very short hairs average; of 0.2 mm in length and to small to be measured with RHS-CC.

*Buds*.—Flattened globular in shape, up to 2.2 cm in diameter and 1.7 cm in height, 143A, immature ray florets 150B to 150C.

*Peduncle*.—Strong, continuous with stem, average angle of secondary and tertiary peduncles 10°, 14.1 cm in length and an average of 4 mm in diameter, 144B in color, surface is covered with very short strigose hairs, 0.3 mm in length and to small to measure with RHS-CC.

*Ray florets*.—Rotate, about 24, oblanceolate in shape, about 3.3 cm in length and 8 mm in width, praemorse apex, cuneate base, entire margin, held at an average angle of 15° upward near horizontal, upper surface texture is smooth and velvety and moderately ribbed lengthways (carinate), lower surface texture is smooth and moderately ribbed lengthways (carinate), color: when opening upper surface; 14A to 14B, when opening lower surface; 11B, when fully open upper surface; 14A, when fully open lower surface; 11B.

*Disc florets* (*bisexual*).—Numerous, about 350, tubular in shape, fused into tube upper 12.5% free, arranged spirally on a conical receptacle, about 1 cm in length and 3 mm in width, entire margin, upper and lower surfaces smooth and glossy in appearance, color of upper and lower surfaces when opening; 145C, color of upper and lower surfaces when fully open; 144A, mid-section 145C.

*Receptacle*.—Broad triangular in shape, about 1.2 cm in diameter and 1 cm in height, color 155D.

*Receptacle spines*.—Average of 350, acicular in shape, acute apex, attenuate base, smooth and glossy surface, color: apex; 14A, mid-section; 143B, base; 138B.

Reproductive organs:

*Gynoecium*.—Pistil; 1, 7 mm in length, style; 5 mm in length and 145C in color, ovary; between 145D and 157D in color.

*Androcoecium*.—Stamens; 4, filament 4 mm in length and 150D in color, anther; linear in shape, 3 mm in length and 200A to 200B in color, pollen; moderate in quantity and 17A to 17B in color.

*Fruit/seed*.—No fruit or seed detected to date.

It is claimed:

1. A new and distinct cultivar of *Echinacea* plant named 'Cleopatra' substantially as herein illustrated and described.

* * * * *